United States Patent [19]

Nád et al.

[11] Patent Number: 5,449,828
[45] Date of Patent: Sep. 12, 1995

[54] PROCESS FOR THE PREPARATION OF PROPARGYL AMMONIUM-CHLORIDE

[75] Inventors: Zsuzsanna Nád; Tamás Kállay; Mária Sziládi; Tibor Montay, all of Budapest, Hungary

[73] Assignee: Chinoin Gyogyszer- Es Vegyeszeti Termekek Gyara Rt., Budapest, Hungary

[21] Appl. No.: 353,816

[22] Filed: Dec. 9, 1994

[30] Foreign Application Priority Data

Nov. 22, 1994 [HU] Hungary ................... 33 42/94

[51] Int. Cl.⁶ .................................. C07C 209/02
[52] U.S. Cl. .............................. 564/376; 564/381
[58] Field of Search .......................... 564/376, 381

[56] References Cited

U.S. PATENT DOCUMENTS

| | | | |
|---|---|---|---|
| 3,429,922 | 2/1969 | Beregi et al. | 564/381 |
| 3,485,874 | 12/1969 | Ecsery et al. | 564/381 |
| 3,496,195 | 2/1970 | Ecsery et al. | 564/381 |
| 4,564,706 | 1/1986 | Ecsery et al. | 564/376 |
| 4,960,797 | 10/1990 | Ecsery et al. | 514/654 |
| 5,008,292 | 4/1991 | Ecsery et al. | 514/654 |

Primary Examiner—Richard L. Raymond
Attorney, Agent, or Firm—Herbert Dubno; Jonathan Myers

[57] ABSTRACT

The present invention relates to a process for the preparation of L-isomer of propargyl-ammonium-chloride derivatives of the formula (I)

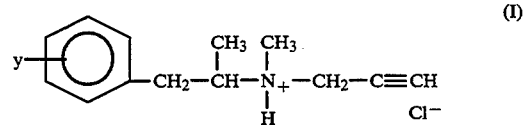

by decomposing D-tartarte of L-isomer of the amine of the general

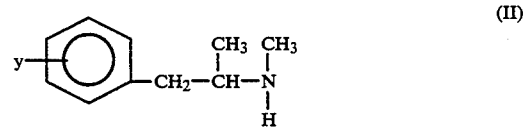

wherein y is hydrogen or fluoro and by reacting the obtained L-issomer amine of the formula (II) in the presence of a base with a halide of the formula (V), X—CH₂—C≡CCH wherein X is halogen and by reacting the so obtained L-isomer of the Formula (III)

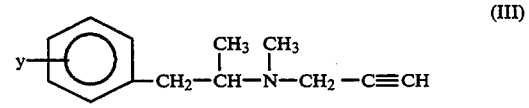

with hydrogen-chloride in an organic solvent, wherein x is a halogen atom,
y is a hydrogen or fluorine atom.

3 Claims, No Drawings

PROCESS FOR THE PREPARATION OF PROPARGYL AMMONIUM-CHLORIDE

SPECIFICATION

1. Field of the Invention

The present invention is directed to an environment saving process for the preparation of 1-N-methyl-N-(2-phenyl-1-methyl)-ethyl-N-propargyl-amine-hydrochloride of the formula (Ia)

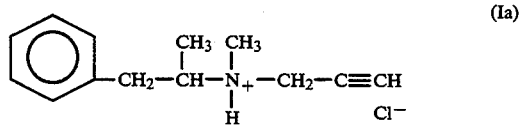

(Ia)

2. Background of the Invention hereinafter Selegiline HCl—and of 1-N-methyl-N-(2-(4-fluoro-phenyl)-1) -methyl)-ethyl-N-propargyl-amine-hydrochloride of the formula (Ib)

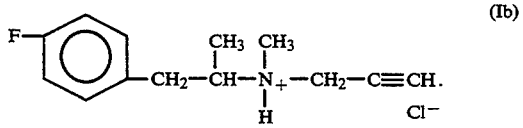

(Ib)

hereinafter p-fluoro-Selegiline-HCl—with good yield and in contamination-free form.

The preparation of propargyl-amine derivatives corresponding to the formula (I)

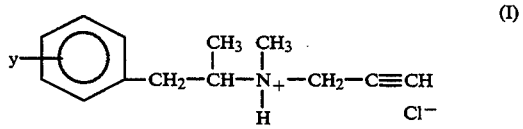

(I)

wherein y is hydrogen of fluoro has been referred to several times in the technical literature. A part of the known processes follows a substantially different reaction scheme compared to the processes disclosed in the present specification. The starting materials of other known processes correspond to the reactants of our process.

The synthesis of the compound corresponding to formula (Ia) but without optical activity has been referred to in Hungarian Patent Specification No. 151,090. The racemic form of the formula (Ia) has been prepared by several processes. According to Examples 1 and 2 of the above reference 1,3-dibromo-propene is added to N-(2-phenyl-1-methyl)-ethyl-N-methyl-amine and the reaction mixture is heated at 100° C. for 7 hours. In the first step of the reaction N-(2-phenyl-1-methyl)-ethyl-N-methyl-N-(2-bromo-propenyl)-amine is obtained which is treated with lye after isolation.

After distillation N-methyl-N-(2-phenyl-1-methyl)-ethyl-N-propargyl-amine is obtained with a yield of 20% related to the starting amine and with a yield of 40% related to the used 1,3-dibromo-propene. According to Example 7, N-methyl-N-(2-phenyl-1-methyl)-ethyl-amine is reacted with propargyl-aldehyde in an alcoholic medium in the presence of aluminum-metal. After adding lye to the reaction mixture, the desired N-propargyl-amine derivative is obtained with a yield of 48.6%.

Another known process is disclosed in the process according to Example 11. The condensation is carried out with 2-phenyl-1-methyl-ethyl-chloride and with N-methyl-N-propargyl-amine under pressure. The reaction mixture is treated with alkali and the desired product is obtained with a yield of 35%.

In Example 5 of the Hungarian patent specification No. 151,090 a process is disclosed which is similar to our process considering the starting materials. To 0.2 mole of N-methyl-N-(2-phenyl-1-methyl)-ethyl-amine 0.1 mole of propargyl-bromide is added, and the reaction mixture is heated at 100° C. for 2 hours. Half the amount of the starting amine is consumed for binding the formed hydrogen bromide. Although the yield of the reaction is 85% of racemic product related to propargyl bromide, the process as a whole is not favorable from a practical point of view as pointed out in the evaluation disclosed on page 2 of Hungarian patent specification No. 187,775. As for the recovery of the expensive amine used as an acid binding agent, benzoylation, followed by separation and hydrolysis are suggested without mentioning the yield of the recovery.

The preparation of optically active propargyl amine derivatives of the formula (Ia) according to our application has been first disclosed in the Examples of Hungarian patent specification No. 154,655 without yield data. According to the process disclosed in Example 5, N-methyl-N-(2-phenyl-1-methyl)-ethyl-amine is reacted with paraformaldehyde followed by acetylene gas in the presence of CuCl$_2$ catalyst. The optically active base of the formula (IIIa)

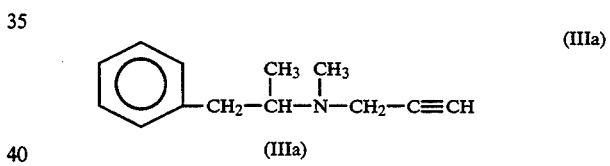

(IIIa)

is obtained with a yield of about 20%.

Example 1 of the above patent specification is also worth mentioning as a water in-soluble solvent has been first used here as medium and the reaction with propargyl-bromide was carried out at 50°–60° C. No active binding agent has been used in the reaction and the released hydrogen bromide has been bound with an excess of the amine.

On the basis of the Examples of the mentioned two Hungarian patent specifications it is obvious that there was no process available which could result on an industrial scale in a good yield of the compound of the formula (Ia). The inventors of Hungarian patent specification No. 187,775 wanted to eliminate these disadvantages.

As a new practice they did no longer use an excess of the starting N-methyl-N-(2-phenyl-1-methyl)-ethyl-amine for acid binding because the recovery of the amine could not be effectively solved. According to their process they released the optically active base from L-N-methyl-N-(2-phenyl-1-methyl)-ethyl-amine-d-tartarate prepared in the course of resolution—hereinafter L-methyl-anara-D-tartarate. This process was performed by adding water to the above tartarate salt and by alkalizing it strongly with an aqueous alkali solution (in the Examples exclusively 40% sodium hydroxide was used) to a pH of 13 and the released amine base was extracted with a water immiscible solvent from the aqueous solution. In order to extract the amine base most completely, the aqueous layer was further extracted. As water-immiscible solvents apolar solvents were used, such as benzene, toluene, dichloroethane, diisopropyl-ether. The alkylation was carried out by reacting 1-N-methyl-N-(2-phenyl-1-methyl)-ethyl-amine—hereinafter 1-methylanara—dissolved in an organic solvent with propargyl-bromide at 55°–60° C. The alkylation reaction carried out in an organic solvent at 50°–60° C. with propargyl-bromide was first mentioned in Example 1 of the Hungarian patent specification No. 154,655. From Hungarian patent specification No. 187,775 one can further see that the novelty of the process comprises in using an aqueous alkali solution as an acid binding agent for binding the hydrogen bromide release during alkylation and the reaction medium is water-solvent emulsion.

The alkylation reaction mixture is worked up by separating the organic solvent layer and washing with water. This organic solvent layer contains unreacted starting materials and by-products next to the base of the formula (IIIa). The amine bases being more alkaline than the amine of the formula (IIIa) in the solvent layer can be removed by extracting with aqueous acids. As an acid, inorganic acids of an acid exponent of 1.0–2.12 or organic acids of an acid exponent of 3.75–4.87 are employed and in order to reduce the dissolution of the main product a method analogous to titration is used. The base of the formula (IIIa) thus purified is dissolved in a water-immiscible solvent, treated with ethylalcohol in hydrochloric acid and a part of the obtained solvent mixture is distilled off and cooled, whereafter the crystalline hydrochloride of the formula (I)

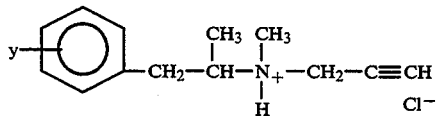

(I)

is obtained. Maximal yield is 65% (Example 1).

Summarizing the process disclosed in Hungarian patent specification No. 187,775 one can see that it was a certain development as compared to Example 5 of the Hungarian patent specification No. 151,090 according to which the racemic Selegiline-base of the formula (IIIa) was obtained in distilled form with a yield of 85% related to propargyl bromide but related to the more valueable methyl-anara the yield was only 43%.

According to Examples of European patent application No. 0,344,675 the product of the formula (Ia) was prepared in anhydrous solvents in the presence of potassium carbonate acid binding agent by alkylation and the product was obtained with a yield of max. 56.6% after complicated purification operations. This was a step backward compared to the known processes.

According to European patent application No. 0,186,680 the desired product is 1-p-fluoro-Selegiline.HCl. The alkylation starting from a racemic amine, an optically active amine, respectively, from 1-p-flouro-methylanara-d-tartarate and propargyl-bromide is performed in each Example in the presence of an anhydrous solvent and potassium carbonate as an acid binding agent or in a water solvent emulsion reaction medium by using sodium-hydroxide as acid binding agent. Maximal yield is 47.1% (Example 5).

OBJECT OF THE INVENTION

The object of the invention is to provide a process which the compounds of the formula (I) could be prepared with good yield with a simple and environment-protecting method in very pure form.

SUMMARY OF THE INVENTION

Surprisingly we have found that if we do not use an organic solvent during the release of the base of the formula (II)

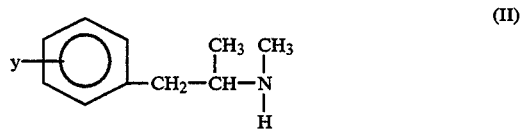

(II)

and during the propargylation reaction but we use as reaction medium and as acid binding agent an aqueous tartaric acid buffer system comprising of ammonium hydroxide or basic alkali salts and/or ammonium salts the pH of which is 8–12, the propargylation reaction can be carried out with high-conversion without separating the base of the formula (II). The moderate pH level used and the low reaction temperature of 0°–50° C. result that the non-desired side-reactions are significantly reduced and thereby the small amount of starting material and contamination can be removed by extraction with ammonium-hydroxide and water or by a selective salt formation method. Our process enables us also to obtain the salts of the formula (I) with excellent yield from such solvent, the use of which was not possible in the known processes, because of the quality of the obtained material.

The advantages of our process can be summarized as follows.

The release of the optically active secondary amine is performed in the alkylation reaction mixture thereby the solvent extraction and the layer separation operations are not needed and there is loss in the yield and no damage in the environment (Hungarian patent specification No. 187,775).

In the propargylation reaction we do not use any solvent dilution or alkali hydroxide acid binding agent but the alkylation is carried out in a tartaric acid buffer mixture ensuring pH 8–12 at 0°–50° C. The reaction conditions result that the obtained amine base of the formula (III)

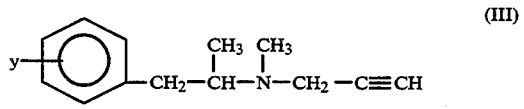

(III)

hardly contains any contaminations or starting materials.

The purity of the obtained amine base of the formula (III) referred according to the process of the invention makes it possible that the remaining small amount of starting material and side-product can be removed by aqueous or ammonia-aqueous extraction or by the very selective and simple double-salt formation technology. For the purpose acid salts of the formula (IV)

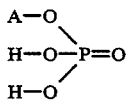

are used in the form of aqueous solution. In the formula A+ stands for sodium, potassium or ammonium ion. The acid salts of the formula (IV) show a very low acidity, Pka=7.21, this is the acid dissociation exponent, and consequently when using the purification method of our process there is no danger of the dissolution of the amine base of the formula (III) because the basicity of the compounds is too low for the salt formation. Inorganic acids—PKa=1.0–2.12—acid dissociation value—and organic acids PKa=3.75–4.87—acid dissociation value—applied for purification according to Hungarian patent specification No. 187,775—are strong or moderately strong acids, the use of which results in the dissolution of the main product of the formula (III).

A further advantage of the process according to the present invention is that there is no need to use a water-immiscible solvent, such as benzene or toluene, in order to recover the end-product of the formula (I), the use of which solvents is a big disadvantage from the point of view of industrial applicability, recovery and health and from an environmental point of view. In developed countries with quality prescriptions, due to strict solvent residual test, pharmaceutical basic materials obtained from water-immiscible solvents can not be used, anyway. When using our process we can use instead of the solvent mixture with disadvantages a water-soluble solvent, preferably acetone or isopropanol in order to obtain the compounds of the formula (I). The use of an acetone reaction medium is additionally advantageous due to its selective dissolving ability solving activity and by retaining the contaminating materials being present in a minimal amount we can obtain a product of purity far above the quality requirements. The purity measured by a HPLC method is a minimum 99.9% and the known and unknown contaminations are below 0.1%.

Selegiline-hydrochloride can be prepared according to the process of the present invention with a very good yield of about 91%. The best yield in the references is 85% (Example 5 of Hungarian patent specification No. 151,090) but this is a value calculated on the alkylation agent achieved by using a double excess of methyl-anara base related to Selegiline base of the formula (IIIa) of non-defined quality. We refer again to page 2 of the Hungarian patent specification 187,775 according to which a 40–50% loss can be calculated during the recovery of the excess amine, making thereby this process very uneconomical. According to Hungarian patent specification No. 187,775 L-methyl-anara excess was no longer used, but the yield value significantly decreased. The best yield related to the starting material L-methyl-anara-D-tartarate amounted to 65% (Example 1). From the mother lye and the washing liquids a further 7.6–19% product was obtained but the components of this product were not given and one can also not determine what working up is needed to get a product corresponding to the first generation. According to our experiences this yield is only approximately 30%.

The maximal yield of Example 5 related to the preparation of p-fluoro-Selegiline HCl in European patent application No. 0,186,680 is only 47.1% as opposed to the 85% achieved in our present process.

The present invention relates to a process for the preparation of L-isomer of a propargyl ammonium-chloride derivatives of the formula (I) by decomposing the D-tartarate of L-isomer of the amine of the formula (II) with a base followed by reacting the L-isomer amine of the formula (II) with a halide of the formula (V)

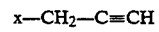

in the presence of a base and by reacting the so-obtained L-isomer of the formula (III ) with hydrogen-chloride in an organic solvent, wherein
  x stands for a halogen atom,
  y stands for a hydrogen or fluorine atom and the process is characterized by releasing the amine base from the D-tartarate of L-isomer of the amine of the formula (II)—wherein y is as given above—in aqueous suspension with ammonium hydroxide or basic alkaline salt and/or ammonium salt, and reacting each in a buffer-system directly formed in the course of the release of base of a pH of 8–12 with a halide of the general formula (V), wherein x is as defined above—
  at 0°–50° C. and after separation of the aqueous layer extracting the mixture containing the L-isomer amines of the formulae (II) and (III) in the organic layer with water with a mixture of ammonium hydroxide and water and/or with an aqueous phosphate salt solution of a pH of 5.5–7.5 and dissolving the L-isomer amine of the formula (II) or salt thereof in the aqueous layer and selectively isolating it from the L-isomer amine of the formula (III) and converting the L-isomer amine of the formula (III) after distillation to the L-isomer salt of the formula (I) by a method known per se.

The details of the process of the invention are illustrated by the following Examples.

EXAMPLE 1

149.7 g (0.5 mole) of L-methyl-anara-O-tartarate, 210 g of concentrated ammonium-hydroxide are admixed and stirred at 20°–25° C. for 10 minutes. 65.5 g (0.55 mole) of propargyl-bromide are added and stirred for 3 hours at 30°–35° C. 210 ml of water are added and the layers are separated at 20°–25° C.

The oily layer is stirred with a mixture of 25 ml water and 25 g of concentrated ammonium hydroxide followed by 50 ml of water and separated. The upper layer (Selegiline-base) is distilled off in vacuo at pressure of 0.1–0.2 kPa. The distilled material is dissolved in 300 ml of acetone and it is adjusted to pH 2–2.5 by introducing hydrochloric acid gas at 20°–30° C. The suspension is crystallized for 2 hours at −10° C., filtered, washed with acetone and dried. 101.8 g L-N-methyl-N-(2-phenyl-1-methyl)-ethyl-N-propargyl amine hydrochloride are obtained, yield: 91%. Purity on the basis of HPLC analysis is 99.9%. Known and unknown total contamination is less than 0.1%.

EXAMPLE 2

149.7 g (0.5 mole) of L-methyl-anara-D-tartarate, 210 ml of water and 210 g of concentrated ammonium hydroxide are admixed and after stirring for 10 minutes 65.5 g (0.55 mole) of propargyl bromide are added at 20°–25° C. The mixture is stirred at 30°–35° C. for 1 hour, and at 40°–45° C. for another hour. Cooling back to 20°–25° C. the layers are separated and we may proceed as disclosed in Example 1.

Yield: 100.7 g Selegiline HCl, 90%.

The quality of the product is corresponds to the product obtained in Example 1.

EXAMPLE 3

One may proceed as disclosed in Example 2 and the obtained alkylation reaction mixture is separated at 20°–25° C. The upper layer is shaken out with 2×25 ml of water followed by 2×30 g of 10% by weight of sodium dihydrogen phosphate solution and then with 25 ml of water. The mixture is separated. The upper layer is distilled off as disclosed in Example 1 and worked up. Yield: 98.5 g (88%).

Purity on the basis of HPLC analysis min. 99.8%, the known and unknown contaminations amount to less than 0.05%.

EXAMPLE 4

149.7 g (0.5 mole) of L-methyl-anara-D-tartarate, 175 g of concentrated ammonium hydroxide and 175 ml of water are admixed. After 10 minutes stirring at 20°–25° C. 41.0 g (0.55 mole) of propargyl-chloride are added. One may further proceed as disclosed in Example 1 or 3.

Yield: 95 g (85%).

The quality of the product is identical to that obtained according to Example 1.

EXAMPLE 5

178.6 g, 0.5 mole of p-fluoro-L-methyl-anara-D-tartarate-dihydrate, 210 g of concentrated ammonium-hydroxide, 210 ml of water are admixed and stirred for 10 minutes at 20°–25° C. The mixture is cooled to 0° C. and 65.5 g (0.55 mole) of propargyl-bromide are added. The mixture is stirred at 0°–5° C., and then for 1.5 hours at 20°–25° C. The layers are separated. The upper oily layer is shaken out with 2×30 g of saturated sodium-chloride solution and 2×30 g of sodium-dihydrogen-phosphate solution of 10% by weight followed by 2×30 g of saturated sodium-chloride solution and separated. The upper layer (p-fluoro-Selegiline-base) is distilled off in vacuo at a pressure of 0.1–0.2 kPa. The distilled material is dissolved in 300 ml of acetone and adjusted to pH 2.5 by introducing hydrochloric acid gas at 15°–25° C. The suspension is crystallized for 2 hours at −10° C. filtered, washed with acetone and dried. The product is 102.3 g of p-fluoro-Selegiline-hydrochloride, yield: 85%.

Purity according to HPLC analysis: 99.9%. The known and unknown contaminations amount to less than 0.1%.

EXAMPLE 6

149.7 g (0.5 mole) L-methyl-anara-D-tartarate, 750 ml of water and 414.6 g (3.0 mole) of potassium-carbonate are admixed and stirred for 10 minutes at 30°–35° C. 65.5 g (0.55 mole) of propargyl-bromide are added and stirred for an hour at 35°–40° C. and for another hour at 40°–45° C. The mixture is cooled back to 20°–25° C. and the lower layer is separated. The upper oily layer is admixed with 5×50 ml water, separated and the upper layer is distilled and worked up according to Example 1.

Yield.: 101.8 g Selegiline HCl, 91%.

Purity according to HPLC analysis: 99.9%. The known and unknown contaminations amount to less than 0.1%.

EXAMPLE 7

149.7 g (0.5 mole) of L-methyl-anara-D-tartarate 750 ml of water and 318.0 g (3 mole) of sodium-carbonate are admixed and stirred for 10 minutes at 30°–35° C. 65.5 g (0.55 mole) propargyl-bromide are added and stirred for 1 hour at 35°–40° C. for half an hour at 45°–50° C. After cooling back to 20°–25° C. the lower layer is separated. The upper oily layer is admixed with 5×50 ml of water and separated. The upper layer is distilled and worked up to Selegiline HCl salt according to Example 1.

Yield: 101.8 g, 91%.

Purity according to HPLC analysis: 99.9%. The known and unknown contaminations amount to less than 0.1%.

EXAMPLE 8

The alkylation reaction mixture obtained according to Example 6 or 7 is separated at 20°–25° C. The upper layer is shaken out with 2×50 ml of water, followed by 2×30 g of sodium-dihydrogen-phosphate solution of 10% by weight and separated. The upper layer is distilled according to Example 1 and worked up.

Yield: 99.5 g, 89%.

Purity according to HPLC analysis: 99.9%. The known and unknown contaminations amount to less than 0.05%.

EXAMPLE 9

88.3 g (0.25 mole) of p-fluoro-L-methyl-anara-D-tartarate-dihydrate, 375 ml of water and 138.2 g (1 mole) of potassium carbonate are admixed and stirred for 10 minutes at 30°–35° C. The mixture is cooled to 10°–15° C. 35.7 g (0.3 mole) of propargyl-bromide are added and stirred at 15°–20° C. for 30 minutes and 2.5 hours at 20°–25° C. The layers are separated. The upper oily layer is shaken out with 25 ml of water, 25 g of saturated sodium chloride solution, 2×15 g of 10% by weight of sodium dihydrogen phosphate solution and 2×25 g of saturated sodium chloride solution and separated. The upper oily layer (p-fluoro-Selegiline-base) is distilled off in vacuo at 0.1–0.2 kPa pressure. The distilled material is dissolved in 150 ml of acetone and adjusted to pH 2.5–3.5 by introducing hydrochloric acid gas at 15°–25° C. The suspension is crystallized for 2 hours at −10° C., filtered and washed with acetone and dried. The product is 45.3 g of p-fluoro-Selegiline-hydrochloride, yield: 75%.

Purity according to HPLC analysis: 99.9%. The known and unknown contaminations amount to less than 0.1 %.

EXAMPLE 10

88.3 g (0.25 mole) of p-fluoro-L-methyl-anara-D-tartarate-dihydrate, 375 ml of water and 159.0 g (1.5 mole) of sodium-carbonate are admixed and stirred for 10 minutes at 30°–35° C. One may further proceed according to Example 9 and the mixture is worked up.

Yield: 45.3 g (75%).

The quality of the product corresponds to the quality of that obtained according to Example 9.

EXAMPLE 11

88.3 g (0.25 mole) of p-fluoro-L-methyl-anara-D-tartarate-dihydrate, 105 g of concentrated ammonium-hydroxide, 105 g of water are admixed and stirred at 20°–25° C. for 10 minutes. The mixture is cooled to 5°–10° C. and 32.8 g (0.275 mole) of propargyl-bromide are added. The mixture is stirred for one hour at 5°–10° C. and for 1 hour at 20°–25° C. and for 1 hour at 40°–45° C. The layers are separated, the upper oily layer is shaken out with a mixture of 2×25 ml of water and 25 ml of concentrated ammonium-hydroxide and 2×25 g of saturated sodium chloride solution and separated. The mixture is further worked up according to Example 9.

Yield: 48.3 g (80%).

The quality of the product corresponds to the quality of that obtained according to Example 9.

EXAMPLE 12

88.3 g (0.25 mole) of p-fluoro-L-methyl-anara-D-tartarate-dihydrate are stirred in 105 g of concentrated ammonium-hydroxide for 10 minutes at 20°–25° C. The mixture is cooled to 5°–10° C. and 32.8 g (0.275 mole) of propargyl-bromide are added. The mixture is stirred for an hour at 5°–10° C. and for an hour at 25°–30° C. and the layers are separated. The upper oily layer is shaken out with 25 ml of water, 25 g of saturated salt solution, 2× 15 g of sodium-dihydrogen-phosphate of 9% by weight and disodium-hydrogen-phosphate of 1% by weight and with 25 g of saturated sodium-chloride solution and separated. The mixture is further worked up according to Example 9.

Yield: 48.3 g (80%).

The quality of the product corresponds to the quality of that obtained according to Example 9.

EXAMPLE 13

88.3 g (0.25 mole) of p-fluoro-L-methyl-anara-D-tartarate-dihydrate, 105 g of concentrated ammonium-hydroxide and 105 g of water are admixed and stirred for 10 minutes at 20°–25° C. The mixture is cooled to 5° C. and 32.8 g (0.275 mole) of propargyl-bromide are added. The mixture is stirred for half an hour at 5°–10° C. and for 1.5 hours at 25°–30° C. The mixture is cooled to 20°–25° C., the layers are separated. The upper oily layer is shaken out with 25 ml of water, 25 g of saturated sodium-chloride solution, 2×15 g of aqueous solution containing disodium-hydrogen-phosphate of 2% by weight and sodium-dihydrogen-phosphate of 8% by weight and with 25 g of saturated sodium-chloride solution and separated. The upper layer (p-fluoro-Selegiline-base) is distilled in vacuo at a pressure of 0.1–0.2 kPa. The distilled material is dissolved in 150 ml of isopropyl-alcohol and the pH is adjusted to 3.0–3.5 by adding hydrochloric acid at 15°–25° C. The suspension is crystallized for 2 hours at −10° C., filtered, washed with isopropyl alcohol and dried.

48.3 g (80%) of p-fluoro-Selegiline-hydrochloride are obtained. The quality of the product corresponds to the quality of that obtained according to Example 9.

What is claimed is:

1. Process for the preparation of L-isomer of propargyl-ammonium-chloride derivatives of the formula (I)

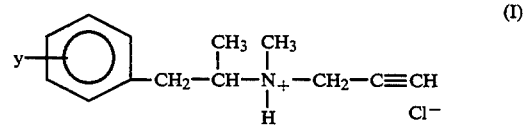

by decomposing D-tartarate of L-isomer of the amine of the formula (II)

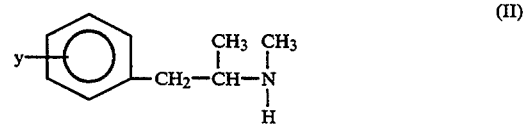

and by reacting the obtained L-isomer amine of the formula (II) in the presence of a base with a halide of the formula (V), and by reacting the so-obtained L-isomer of the formula (III)

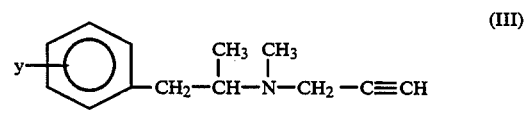

with hydrogen-chloride in an organic solvent, wherein
x is a halogen atom,
y is a hydrogen or fluorine atom
which comprises releasing the amine base from the D-tartarate of the L-isomer of the amine of the general formula (II), in aqueous suspension with ammonium hydroxide or basic alkaline salt and/or ammonium salt, and reacting same with 1–1.5 mole equivalent of a halide of the formula (V),

wherein
x is as defined above—at 0°–50° C. in a buffer system of the pH of 8–12 directly formed in the course of the base release and after separating the aqueous layer extracting the mixture containing L-isomer amines of the formulae (II) and (III) in the organic layer with water and with a mixture of ammonium hydroxide and water and/or with a solution of aqueous phosphate salt of a pH of 5.5–7.5 and dissolving the L-isomer amine of the general formula (II) or salts thereof into the aqueous layer and selectively separating it from the L-isomer amine of the general formula (III) and converting the L-isomer amine of the formula (III) after distillation to L-isomer salt of the formula (I).

2. Process according to claim 1 which comprises using as a phosphate-salt a monobasic phosphate-salt of the formula (IV),

wherein A+ is sodium, potassium or ammonium ion.

3. A process as claimed in claim 1 which comprises using as organic solvent acetone or isopropanol in order to recover the salt of the formula (I).

* * * * *